(12) United States Patent
Underhill et al.

(10) Patent No.: US 7,612,249 B2
(45) Date of Patent: Nov. 3, 2009

(54) DISPOSABLE ABSORBENT ARTICLE

(75) Inventors: Richard L. Underhill, Neenah, WI (US); Michael J. Niemeyer, Appleton, WI (US); Marianne K. Leick, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 845 days.

(21) Appl. No.: 10/857,090

(22) Filed: May 28, 2004

(65) Prior Publication Data

US 2004/0220540 A1    Nov. 4, 2004

Related U.S. Application Data

(62) Division of application No. 10/022,328, filed on Dec. 14, 2001, now Pat. No. 6,958,432.

(51) Int. Cl.
*A61F 13/20* (2006.01)
(52) U.S. Cl. .................. 604/378; 604/379; 604/380; 604/381; 604/382; 604/383
(58) Field of Classification Search .......... 604/378–383
See application file for complete search history.

(56) References Cited

U.S. PATENT DOCUMENTS

| | | | |
|---|---|---|---|
| 2,043,325 A | 6/1936 | Jackson, Jr. | |
| 3,769,978 A | 11/1973 | DeNight et al. | |
| 3,888,257 A | 6/1975 | Cook et al. | |
| 4,041,950 A | 8/1977 | Jones, Sr. | |
| 4,285,342 A | 8/1981 | Mesek | |
| 4,306,559 A * | 12/1981 | Nishizawa et al. | .......... 604/371 |
| 4,324,247 A | 4/1982 | Aziz | |
| 4,381,783 A | 5/1983 | Elias | |
| 4,461,621 A | 7/1984 | Karami et al. | |
| 4,906,243 A | 3/1990 | Dravland | |
| 4,940,464 A * | 7/1990 | Van Gompel et al. | ....... 604/396 |
| 5,047,023 A | 9/1991 | Berg | |
| 5,062,839 A | 11/1991 | Anderson | |
| 5,342,343 A | 8/1994 | Kitaoka et al. | |
| 5,370,632 A | 12/1994 | Beplate | |
| 5,451,442 A | 9/1995 | Pieniak et al. | |

(Continued)

FOREIGN PATENT DOCUMENTS

EP    0 217 666 A2    4/1987

(Continued)

*Primary Examiner*—Tatyana Zalukaeva
*Assistant Examiner*—Ginger T Chapman
(74) *Attorney, Agent, or Firm*—Armstrong Teasdale, LLP

(57) ABSTRACT

A disposable absorbent article has a liner, an outer cover and an absorbent body therebetween for absorbing liquid body waste penetrating the liner. A flow control layer having lateral side edges is positioned between the liner and the absorbent body, with at least a portion of each lateral side edge of the flow control layer spaced laterally inward from lateral side edges of the absorbent body. The flow control layer is at least in part liquid impermeable to retard the flow of liquid body waste penetrating the liner toward the absorbent body whereby at least a portion of the liquid body waste that penetrates the liner is directed by the flow control layer to migrate laterally outward toward the lateral side edges of the flow control layer for subsequent flow around the flow control layer toward the absorbent body.

5 Claims, 5 Drawing Sheets

U.S. PATENT DOCUMENTS

| | | |
|---|---|---|
| 5,476,458 A | 12/1995 | Glaug et al. |
| 5,649,914 A | 7/1997 | Glaug et al. |
| 5,658,268 A | 8/1997 | Johns et al. |
| 5,681,298 A | 10/1997 | Brunner et al. |
| 5,904,675 A * | 5/1999 | Laux et al. ............. 604/385.29 |
| 6,168,849 B1 * | 1/2001 | Braverman et al. ......... 428/137 |
| 6,229,063 B1 * | 5/2001 | Shimoe et al. .............. 604/378 |
| 6,320,096 B1 * | 11/2001 | Inoue et al. ................. 604/378 |
| 6,958,432 B2 | 10/2005 | Underhill et al. |

FOREIGN PATENT DOCUMENTS

| | | |
|---|---|---|
| EP | 0 455 607 A1 | 11/1991 |
| WO | WO 00/09056 A1 | 2/2000 |

* cited by examiner

DISPOSABLE ABSORBENT ARTICLE

CROSS-REFERENCE TO RELATED APPLICATION

This patent application is a divisional patent application of U.S. patent application Ser. No. 10/022,328 filed on Dec. 14, 2001, which is incorporated herein in its entirety.

BACKGROUND OF THE INVENTION

The present invention relates to disposable absorbent articles, such as those used as personal care products, and more particularly to such a disposable absorbent article which provides an indication of wetness to the wearer upon the release of liquid body waste into the article.

Disposable absorbent articles find widespread use as personal care products such as diapers, children's toilet training pants and other infant and child care products, adult incontinence garments and other adult care products, sanitary napkins and other feminine care products and the like, as well as surgical bandages and sponges. These articles absorb and contain body waste and are intended to be discarded after a limited period of use; i.e., the articles are not intended to be laundered or otherwise restored for reuse. Conventional disposable absorbent articles comprise an absorbent body disposed between an inner layer adapted for contacting the wearer's skin and an outer layer for inhibiting liquid waste absorbed by the absorbent body from leaking out of the article. The inner layer of the absorbent article is typically liquid permeable to permit body waste to pass therethrough for absorption by the absorbent body.

For example, wearer's toilet training pants serve as a training aid as a child transitions from diapers to underpants. Conventional toilet training pants are three-dimensional articles, similar to underpants in appearance, but constructed with a liquid permeable inner layer and an absorbent body to provide the absorbent function of disposable absorbent articles. An initial step in the toilet training process is for the child to recognize when urination occurs. However, where the training pants quickly and effectively draw urine away from the skin and retain the urine in the absorbent body, the inner layer of the pants remains dry and comfortable against the child's skin. As a result, there is little or no recognizable indication to the child that he or she has urinated. To this end, it is desirable to provide some indication to the child that the child has urinated in the training pants.

Therefore, despite advancements in the construction of disposable absorbent articles, there continues to be a need for relatively easily constructed disposable absorbent articles capable of indicating to the wearer that a release of liquid body waste has occurred.

SUMMARY OF THE INVENTION

In general, a disposable absorbent article of the present invention comprises generally a liquid permeable liner having a bodyfacing surface, an outer cover, and an absorbent body. The absorbent body is disposed between the liner and the outer cover for absorbing liquid body waste and having lateral side edges. A flow control layer is positioned between the liner and the absorbent body and has lateral side edges. At least a portion of each lateral side edge of the flow control layer is spaced laterally inward from the lateral side edges of the absorbent body. The flow control layer is at least in part liquid impermeable to retard the flow of liquid body waste penetrating the liner toward the absorbent body. At least a portion of the liquid body waste that penetrates the liner is directed by the flow control layer to migrate laterally outward toward the lateral side edges of the flow control layer for subsequent flow around the flow control layer toward the absorbent body.

In another embodiment, the flow control layer is constructed to retard the flow of liquid body waste penetrating the liner toward the absorbent body. The flow control layer directs the flow of at least a portion of the liquid body waste that penetrates the liner laterally outward toward the lateral side edges of the flow control layer for subsequent flow around the flow control layer toward the absorbent body. Toilet training pants of the present invention generally comprise an anterior region, a posterior region and a crotch region disposed longitudinally therebetween. The anterior region, posterior region and crotch area are integrally formed and configured to define a central waist opening and a pair of leg openings of the pants. The crotch region extends generally laterally between the leg openings. A generally liquid permeable liner extends from the anterior region through the crotch region to the posterior region of the pants and has a bodyfacing surface, an outer cover, and an absorbent body disposed between the liner and outer cover for absorbing liquid body waste. The absorbent body has lateral side edges. A flow control layer is positioned between the liner and the absorbent body and has lateral side edges. At least a portion of each lateral side edge of the flow control layer is spaced laterally inward from the lateral side edges of the absorbent body. The flow control layer is at least in part liquid impermeable to retard the flow of liquid body waste penetrating the liner toward the absorbent body. At least a portion of the liquid body waste that penetrates the liner is directed by the flow control layer to migrate laterally outward toward the lateral side edges of the flow control layer for subsequent flow around the flow control layer toward the absorbent body.

Other aspects and features of this invention will be in part apparent and in part pointed out hereinafter.

DEFINITIONS

Figure 1:
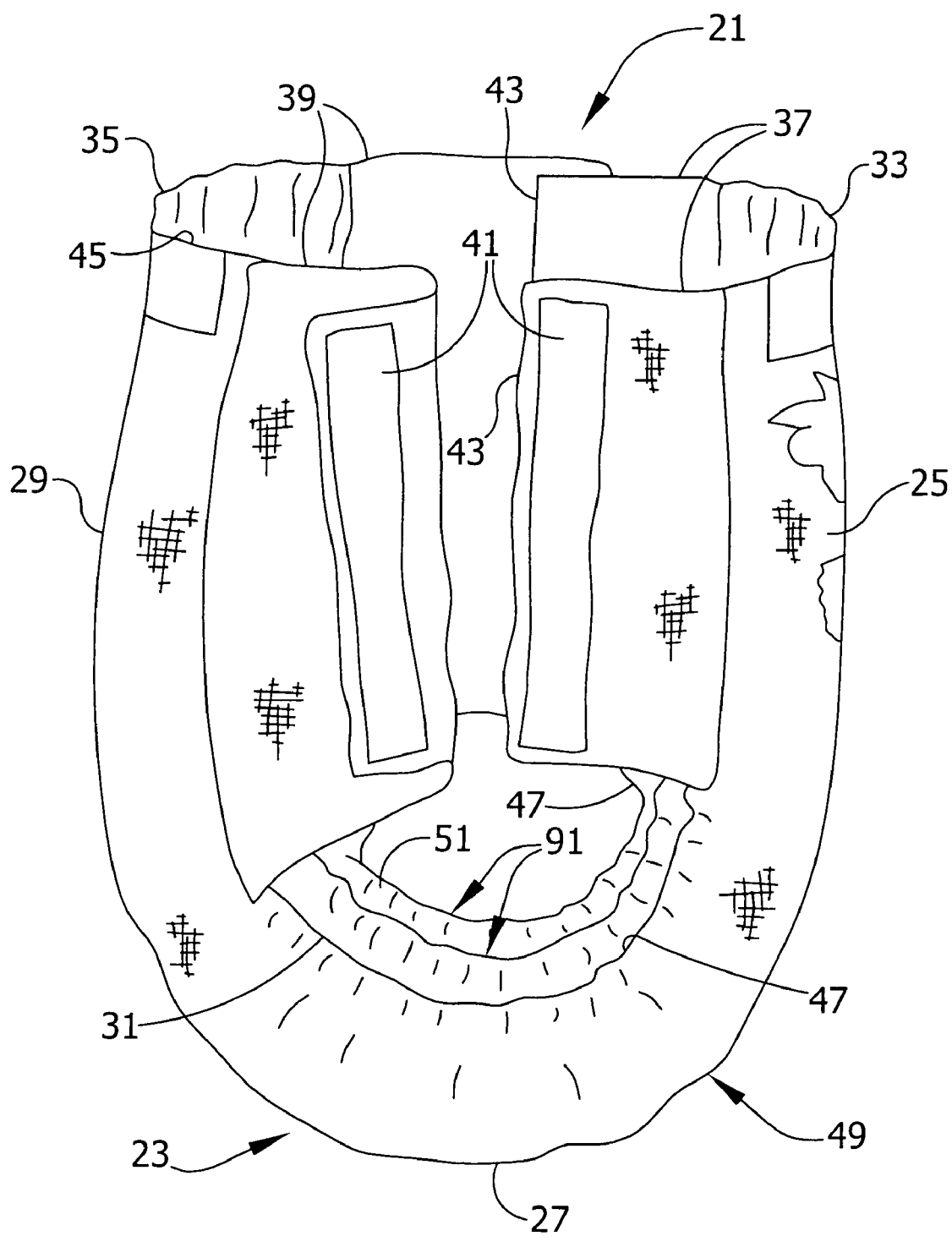
FIG. 1 is a side perspective of wearer's toilet training pants of the present invention.

Within the context of this specification, each term or phrase below will include the following meaning or meanings:

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Hydrophilic" describes fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

"Layer" when used in the singular can have the dual meaning of a single element or a plurality of elements.

"Liquid impermeable" when used in describing a layer or multi-layer laminate means that liquid body waste, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Non-woven" and "non-woven web" refer to materials and webs of material which are formed without the aid of a textile weaving or knitting process.

"Pliable" refers to materials which are compliant and which will readily conform to the general shape and contours of the wearer's body.

"Spunbond" refers to small diameter fibers which are formed by extruding molten thermoplastic material as filaments from a plurality of fine capillaries of a spinnerette having a circular or other configuration, with the diameter of the extruded filaments then being rapidly reduced by a conventional process such as that described in U.S. Pat. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, more particularly, between about 0.6 and about 10.

"Superabsorbent" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surge Layer" refers to a layer capable of rapidly accepting and temporarily holding liquid body waste to decelerate and diffuse a surge or gush of liquid body waste and to subsequently slowly release the liquid body waste therefrom into another layer or layers.

"Thermoplastic" describes a material which softens when exposed to heat and which substantially returns to a non-softened condition when cooled to room temperature.

"Three dimensional" refers to a garment similar to underwear, shorts or pants in that it has continuous leg and waist openings that are bounded by material of which the garment is made. The garment may or may not have manually tearable seams.

DETAILED DESCRIPTION OF THE PREFERRED EMBODIMENTS

Referring now to the drawings and in particular to FIG. 1, a disposable absorbent article of the present invention is shown in the form of wearer's toilet training pants and is indicated in its entirety by the reference numeral 21. As used herein, a disposable absorbent article refers to an article which may be placed against or in proximity to the body (i.e., contiguous to the body) of the wearer to absorb and contain various liquid waste discharged from the body. Such articles are intended to be discarded after a limited period of use instead of being laundered or otherwise restored for reuse. It is understood that the present invention is applicable to various other disposable absorbent articles, such as diapers and other infant and child care products, adult incontinence garments and other adult care products, sanitary napkins and other feminine care products and the like, as well as surgical bandages and sponges, without departing from the scope of the present invention.

By way of illustration only, various materials and methods for constructing training pants 21 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference.

Figure 2:
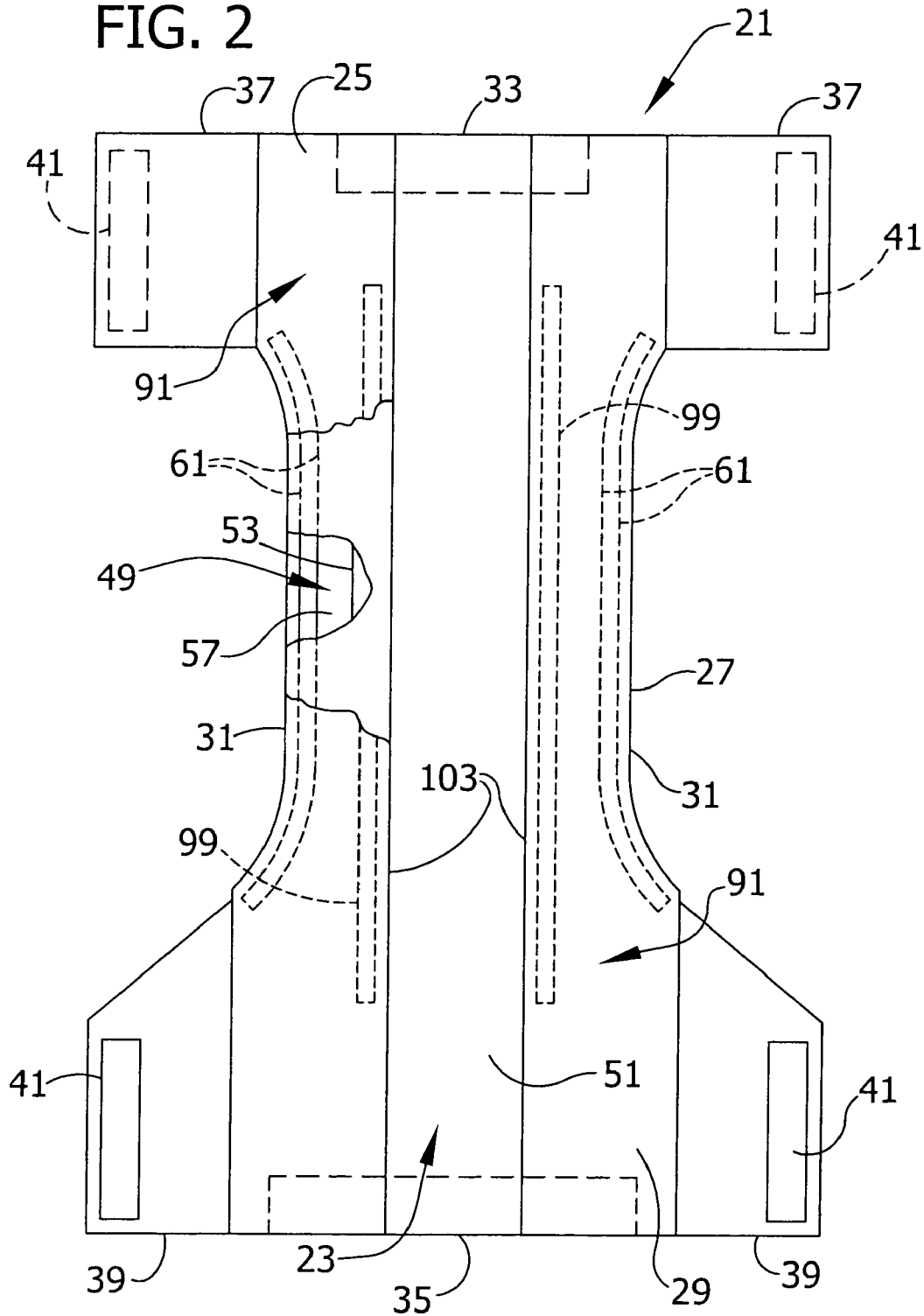
FIG. 2 is a top plan view of the training pants of FIG. 1 with the pants shown unfastened and laid flat and portions of the pants broken away to reveal internal construction thereof.

The training pants 21 of the illustrated embodiment generally comprise a central absorbent assembly 23 extending longitudinally from an anterior region 25 of the training pants through a crotch region 27 to a posterior region 29 of the training pants. As illustrated in FIG. 2, the central absorbent assembly 23 is generally rectangular and has laterally opposite side edges 31 and longitudinally opposite front and rear waist edges, respectively designated 33 and 35. Front and rear side panels 37, 39, respectively, are secured to the central absorbent assembly 23 as will be described later herein and extend laterally outward therefrom respectively at the anterior and posterior regions 25, 29 of the training pants 21.

To form the three-dimensional training pants 21, corresponding front and rear side panels 37, 39 (e.g., the front left side panel and the rear left side panel) are refastenably secured together, using fastening assemblies 41, along generally vertical seams 43. Alternatively, the front and rear side panels 37, 39 may be permanently secured together, such as by ultrasonic bonding, or they may be formed integrally with each other and with the central absorbent assembly 23. Securing the side panels 37, 39 together provides a central waist opening 45 and a pair of laterally spaced leg openings 47 of the training pants 21. The training pants 21 are worn by inserting the wearer's feet through the waist opening 45 and the respective leg openings 47; grasping the training pants near the waist opening; and then pulling the pants up along the wearer's legs until the crotch region 27 of the training pants fits snugly against the crotch of the wearer.

Figure 3:
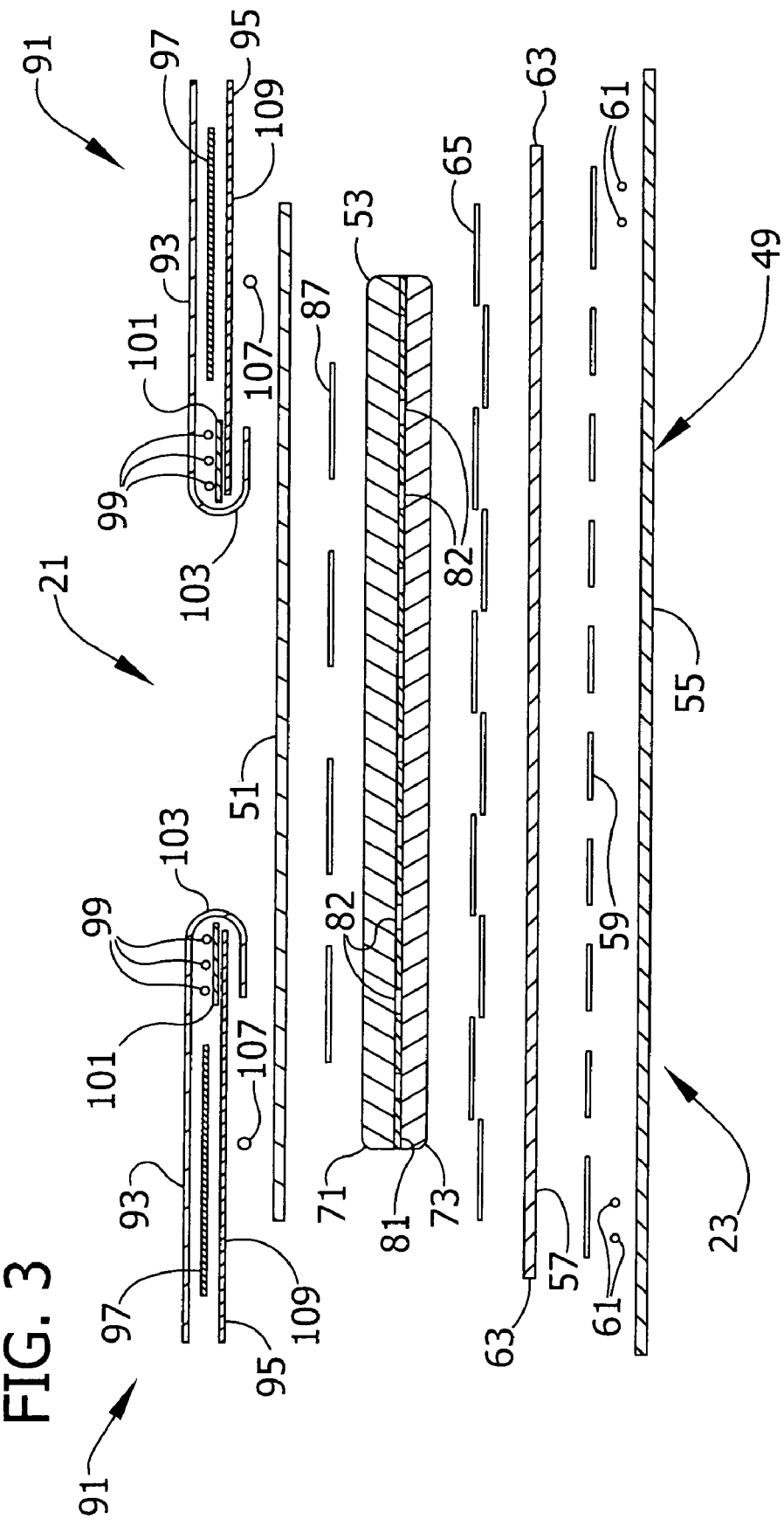
FIG. 3 is a separated cross-section of the training pants of FIG. 1 taken laterally through a crotch region of the pants.

With reference to FIG. 3, the central absorbent assembly 23 of the training pants 21 comprises an outer cover, generally indicated at 49, a bodyside liner 51 and an absorbent body 53 disposed between the outer cover and the liner. The outer cover 49 can be elastic, stretchable or non-stretchable and is desirably a multi-layered laminate structure of which at least one of the layers is liquid impermeable. For example, the outer cover 49 of the illustrated embodiment is of two-layer construction, including an outer layer 55 constructed of a liquid permeable material and an inner layer 57 constructed of a liquid impermeable material joined together by a laminate adhesive 59. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. It is understood that the outer cover 49 may instead be constructed of a single layer of impermeable material without departing from the scope of this invention.

The liquid permeable outer layer 55 of the outer cover 49 can be any suitable material and is desirably one that provides a generally cloth-like texture. One example of such a material is a 20 gsm (grams per square meter) spunbond polypropylene non-woven web. The outer layer 55 may also be constructed of the same materials from which the bodyside liner 51 is constructed as described later herein. Also, while it is not a necessity for the outer layer 55 of the outer cover 49 to be liquid permeable, it is desired that it provide a relatively cloth-like texture to the wearer.

The liquid impermeable inner layer 57 of the outer cover 49 can be either vapor permeable (i.e., "breathable") or vapor impermeable. The inner layer 57 is desirably manufactured from a thin plastic film, although other flexible liquid impermeable materials may also be used. The liquid impermeable inner layer 57 (or the liquid impermeable outer cover 49 where the outer cover is of a single-layer construction) inhibits liquid body waste from leaking out of the pants and wetting articles, such as bed sheets and clothing, as well as the wearer and care giver. A suitable liquid impermeable material for such use is a 0.02 millimeter polyethylene film commercially available from Huntsman Packaging of Newport News, Va., U.S.A.

Where the outer cover 49 is of single-layer construction, it can be embossed and/or matte finished to provide a more cloth-like appearance. As earlier mentioned, the liquid impermeable layer of the outer cover 49 can permit vapors to escape from the pants 21 while preventing liquids from passing therethrough. A suitable liquid impermeable, vapor permeable material is composed of a microporous polymer film or a non-woven fabric which has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn., U.S.A.

Leg elastic members 61 are secured between the outer and inner layers 55, 57 of the outer cover 49, such as by being bonded therebetween by the laminate adhesive 59, generally adjacent laterally outer edges 63 of the inner layer of the outer cover. Alternatively, the leg elastic members 61 may be disposed between the outer cover 49 and the bodyside liner 51, or between other layers of the pants 21. A wide variety of elastic materials may be used for the leg elastic members 61. As is well known to those skilled in the art, suitable elastic materials include sheets, strands or ribbons of natural rubber, synthetic rubber, or thermoplastic elastomeric polymers. The elastic materials can be stretched and secured to a substrate, secured to a gathered substrate, or secured to a substrate and then elasticized or shrunk, for example with the application of heat, such that elastic retractive forces are imparted to the substrate. For example, one suitable elastic material is a dry-spun coalesced multifilament spandex elastomeric thread sold under the trade name LYCRA® and available from E. I. du Pont de Nemours and Company, Wilmington, Del., U.S.A.

The absorbent body 53 is somewhat rectangular and is desirably constructed to be generally compressible, pliable, non-irritating to the wearer's skin and capable of absorbing and retaining liquid body waste, such as urine. In the illustrated embodiment of FIG. 3, the absorbent body 23 comprises an inner layer 71 desirably composed of hydrophilic fibers and an outer layer desirably composed at least in part of a high-absorbency material commonly known as superabsorbent material. More particularly, the inner layer 71 of the absorbent body 53 is desirably composed of cellulosic fluff, such as wood pulp fluff, and the outer layer is desirably composed of superabsorbent hydrogel-forming particles, or a mixture of cellulosic fluff and superabsorbent hydrogel-forming particles. As a result, the inner layer has a lower absorbent capacity per unit weight than the outer layer. The inner layer may alternatively be composed of a mixture of hydrophilic fibers and superabsorbent material, as long as the concentration of superabsorbent material present in the inner layer is substantially lower than the concentration of superabsorbent material present in the outer layer so that the inner layer has a lower absorbent capacity per unit weight than the outer layer. It is also contemplated that the outer layer may be composed solely of superabsorbent material without departing from the scope of this invention.

The cellulosic fluff from which the inner layer 71 is composed desirably has a density of about 0.15-0.20 g/cc (grams per cubic centimeter) and constitutes about 20%-80% by weight of the absorbent body. One suitable type of wood pulp fluff is identified with the trade designation CR1654, available from U.S. Alliance, Childersburg, Ala., U.S.A., and is a bleached, highly absorbent sulfate wood pulp containing primarily soft wood fibers. However, the wood pulp fluff can be exchanged with other hydrophilic fiber materials, such as synthetic, polymeric, or meltblown fibers or with a combination of meltblown fibers and natural fibers.

Suitable superabsorbent materials can be selected from natural, synthetic, and modified natural polymers and materials. The superabsorbent materials can be inorganic materials, such as silica gels, or organic compounds, such as cross-linked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany.

A flow control layer 81 is disposed between the inner and outer layers 71, 73 of the absorbent body 53 to retard the rate at which urine received into the absorbent body passes from the inner layer to the outer layer. The flow control layer 81 shown in FIG. 3 has a width and length substantially the same as the widths and lengths of the inner and outer layers 71, 73 of the absorbent body. However, it is understood that the flow control layer 81 may be narrower and/or shorter than the inner and outer layers 71, 73, or wider and/or longer than the inner and outer layers, without departing from the scope of this invention. The flow control layer 81 may be constructed of either an impermeable material or a permeable material, it being understood that the rate at which urine passes from the inner layer 71 of the absorbent body 53 to the outer layer thereof is generally a function of the permeability of the flow control layer. As an example, one suitable permeable material from which the flow control layer 81 may be constructed is a polypropylene or polyethylene film having apertures 82 formed therein to permit urine to flow therethrough. The apertures 82 are desirably sized in the range of about 1 mm to about 10 mm, and more desirably about 5 mm, and the aperture density of the film is desirably less than or equal to about 14 apertures per square inch of the film. The thickness of the film is desirably less than or equal to about 0.003 inches (i.e., 3 mil).

Another suitable permeable material for construction of the flow control layer 81 is a meltblown, hydrophobic non-woven material. The material desirably has a basis weight of about 0.6 ounces per square yard and a thickness of less than or equal to about 1 mm. It is also contemplated that the flow control layer 81 may be constructed of other permeable materials without departing from the scope of this invention.

As another example, a suitable impermeable material from which the flow control layer 81 may be constructed is a film material, such as a polyethylene or polypropylene film, devoid of apertures to severely retard the flow of urine from the inner layer 71 of the absorbent body 53 to the outer layer 73 thereof. Urine received by the inner layer 71 of the absorbent body 53 is instead directed by the flow control layer 81 to migrate outward (e.g. through the inner layer of the absorbent body) toward the peripheral edges of the flow control layer and then around the edges thereof to the outer layer 73.

The absorbent body 53 may or may not be wrapped or encompassed by a suitable wrapping (not shown) which maintains the integrity and/or shape of the absorbent body. The absorbent body 53 overlays the inner layer 57 of the outer cover 49, extending laterally between the leg elastic members 61, and is secured to the inner layer, such as by being bonded thereto with adhesive 65. However, it is understood that the absorbent body 53 may be unsecured to the outer cover 49 and remain within the scope of this invention.

Still referring to FIG. 3, the bodyside liner 51 overlays the absorbent body 53 to isolate the wearer's skin from liquid body waste retained by the absorbent body and is secured to at least a portion of the absorbent body, such as by being bonded thereto with adhesive 87. The liner 51 further extends beyond the absorbent body 53 to overlay a portion of the inner layer 57 of the outer cover 49, particularly in the crotch region 27 of the pants 21, and is secured thereto, such as by being bonded thereto by adhesive 65, to substantially enclose the absorbent body between the outer cover and the liner about the periphery of the absorbent body. Although the bodyside liner 51 shown in FIG. 3 is slightly narrower than the outer cover 49, it is understood that the liner and outer cover may be of the same dimensions, or the liner may be sized larger than the outer cover, without departing from the scope of this invention. It is also contemplated that the liner 51 may not extend beyond the absorbent body 53 and may not be secured to the outer cover 49 and/or to the absorbent body 53. The bodyside liner 51 is desirably compliant, soft feeling, and non-irritating to the wearer's skin and can be less hydrophilic than the absorbent body 53 to provide a relatively dry surface to the wearer and permit liquid body waste to readily penetrate through its thickness.

The bodyside liner 51 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and non-woven fabrics can be used for the bodyside liner 51. For example, the liner 51 can be composed of a meltblown or spunbonded web of polyolefin fibers. Alternatively, the liner 51 can be a bonded-carded web composed of natural and/or synthetic fibers. The bodyside liner 51 can also be composed of a substantially hydrophobic material, and the hydrophobic material can, optionally, be treated with a surfactant or otherwise processed to impart a desired level of wetability and hydrophilicity. For example, the material can be surface treated with about 0.45 weight percent of a surfactant mixture including AHCOVEL® N-62 available from Uniqema, Inc., a division of ICI of New Castle, Del., U.S.A, and GLUCOPON® 220UP available from Cognis Corporation of Ambler, Pa., U.S.A, in an active ratio of 3:1. The surfactant can be applied by any conventional means, such as spraying, printing, brush coating or the like. The surfactant can be applied to the entire liner 51 or it can be selectively applied to particular sections of the liner.

A particularly suitable bodyside liner 51 is constructed of a non-woven bicomponent web having a basis weight of about 27 gsm. The non-woven bicomponent can be a spunbonded bicomponent web, or a bonded-carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Fibers having other orientations, such as multi-lobe, side-by-side, end-to-end may be used without departing from the scope of the invention. Also, although the outer cover 49 and bodyside liner 51 of the central absorbent assembly 23 can include elastomeric materials, it is contemplated that the central absorbent assembly may instead be generally inelastic, wherein the outer cover; the bodyside liner and the absorbent body 53 are composed of materials which are generally non-elastomeric.

It is also contemplated that other layers (not shown) may lie between the liner 51 and the absorbent 53. For example, a surge layer similar to that disclosed in U.S. Pat. Nos. 5,490,846 and 5,562,650, the entire disclosures of which are incorporated herein by reference, may lie therebetween for quickly absorbing surges of liquid body waste which penetrate the liner, and then slowly releasing the liquid body waste to the absorbent body, without departing from the scope of this invention.

The front and rear side panels 37, 39 of the training pants 21 are bonded to the central absorbent assembly 23 at the respective anterior and posterior regions 25, 29 of the pants and extend outward beyond the laterally opposite edges 31 of the assembly. For example, the front side panels 37 of the illustrated embodiment are secured to the inner layer 57 of the outer cover 49, such as by being bonded thereto by adhesive (not shown), by thermal bonding or by ultrasonic bonding. These side panels 37 may also be secured to the outer layer 55 of the outer cover 49, such as by being bonded thereto by adhesive (not shown), by thermal bonding or by ultrasonic bonding. The rear side panels 39 are secured to the outer and inner layers 55, 57 of the outer cover 49, at the posterior region 29 of the training pants 21, in substantially the same manner as the front side panels 37. Alternatively, the side panels 37, 39 may be formed integrally with the central absorbent assembly 23, such as by being formed integrally with the outer cover 49, the bodyside liner 51 or other layers of the pants 21.

For improved fit and appearance, the side panels 37, 39 desirably have an average length measured parallel to the longitudinal axis of the training pants 21 that is about 20 percent or greater, and more desirably about 25 percent or greater, of the overall length of the training pants, also measured parallel to the longitudinal axis. For example, for training pants 21 having an overall length of about 54 centimeters, the side panels 37, 39 desirably have an average length of about 10 centimeters or greater, and more desirably an average length of about 15 centimeters. Each of the side panels 37, 39 can be constructed of one or more individual, distinct pieces of material. For example, each side panel 37, 39 can include first and second side panel portions (not shown) joined at a seam (not shown), with at least one of the portions including an elastomeric material. Alternatively, each individual side panel 37, 39 can be constructed of a single piece of material folded over upon itself along an intermediate fold line (not shown).

The side panels 37, 39 desirably include an elastic material capable of stretching laterally. Suitable elastic materials, as well as one described process for incorporating elastic side panels 37, 39 into training pants 21, are described in the following U.S. Pat. Nos.: 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. As an example, suitable elastic materials include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panels 37, 39 may include other woven or non-woven materials, such as those described above as being suitable for the outer cover 49 or bodyside liner 51, or stretchable but inelastic materials.

Containment flaps, generally indicated at 91 (FIG. 3), are secured to the body side liner 51 in generally parallel, spaced relation with each other laterally inward of the leg openings 47 to provide a barrier against the flow of urine to the leg openings. The containment flaps 91 extend longitudinally from the anterior region 25 of the training pants 21, through the crotch region 27 to the posterior region 29 of the pants. Each containment flap 91 comprises a non-woven layer 93 and a film layer 95 secured to the non-woven layer, such as by being bonded thereto by adhesive 97. Flap elastics 99 are secured by suitable adhesive 101 between the non-woven layer 93 and the film layer 95 generally at a distal end 103 of the flap 91, with the non-woven layer 93 being folded over the flap elastics 99 and the film layer 95 at the distal end 103. The flap 91 is secured to the bodyside liner 51 by a seam of adhesive 107 to define a proximal end 109 of the flap.

The flap elastics 99 of the illustrated embodiment comprise three individual strands of elastomeric material extending longitudinally along the distal end 103 of the flap 91 in generally parallel, spaced relation with each other. One suitable elastic strand is a LYCRA® T151 940 decitex elastic which can be obtained from E. I. du Pont de Nemours Co. of Wilmington, Del. The elastic strands are secured between the non-woven layer 93 and the film layer 95 while in an elastically contractible condition such that contraction of the strands gathers and shortens the distal end 103 of the containment flap 91. As a result, the elastic strands bias the distal end 103 of each flap 91 toward a position spaced from the proximal end 109 of the flap so that the flap extends away from the liner 51 in a generally upright orientation of the flap, especially in the crotch region 27 of the training pants 21, when the pants are fitted on the wearer. It is understood, however, that the containment flaps 91 may be omitted from the training pants 21 without departing from the scope of the invention.

In use, when the wearer of the training pants 21 urinates therein, urine penetrates the liner 51 and is received in the inner layer 71 of the absorbent body 53 for further flow toward the outer layer 73 thereof. The flow control layer 81 retards the flow of urine to the outer layer 73 of the absorbent body 53, causing unabsorbed urine to be maintained within the inner layer 71, such as in the interstitial spacing of the wood pulp fluff therein, for an extended duration. Maintaining the unabsorbed urine within the inner layer 71 of the absorbent body 53 in this manner facilitates the flow back of urine through the liner 51 to provide a desirably prolonged feeling of wetness against the wearer's skin, thereby providing an indication that urination has occurred. Eventually, urine flows through (if the flow control layer 81 is constructed of a permeable material) and/or around (if the flow control layer is constructed of an impermeable material) the flow control layer to the outer layer 73 for subsequent absorption by superabsorbent material in the outer layer to again provide a dry, comfortable feeling of the liner against the wearer's skin.

Figure 4:
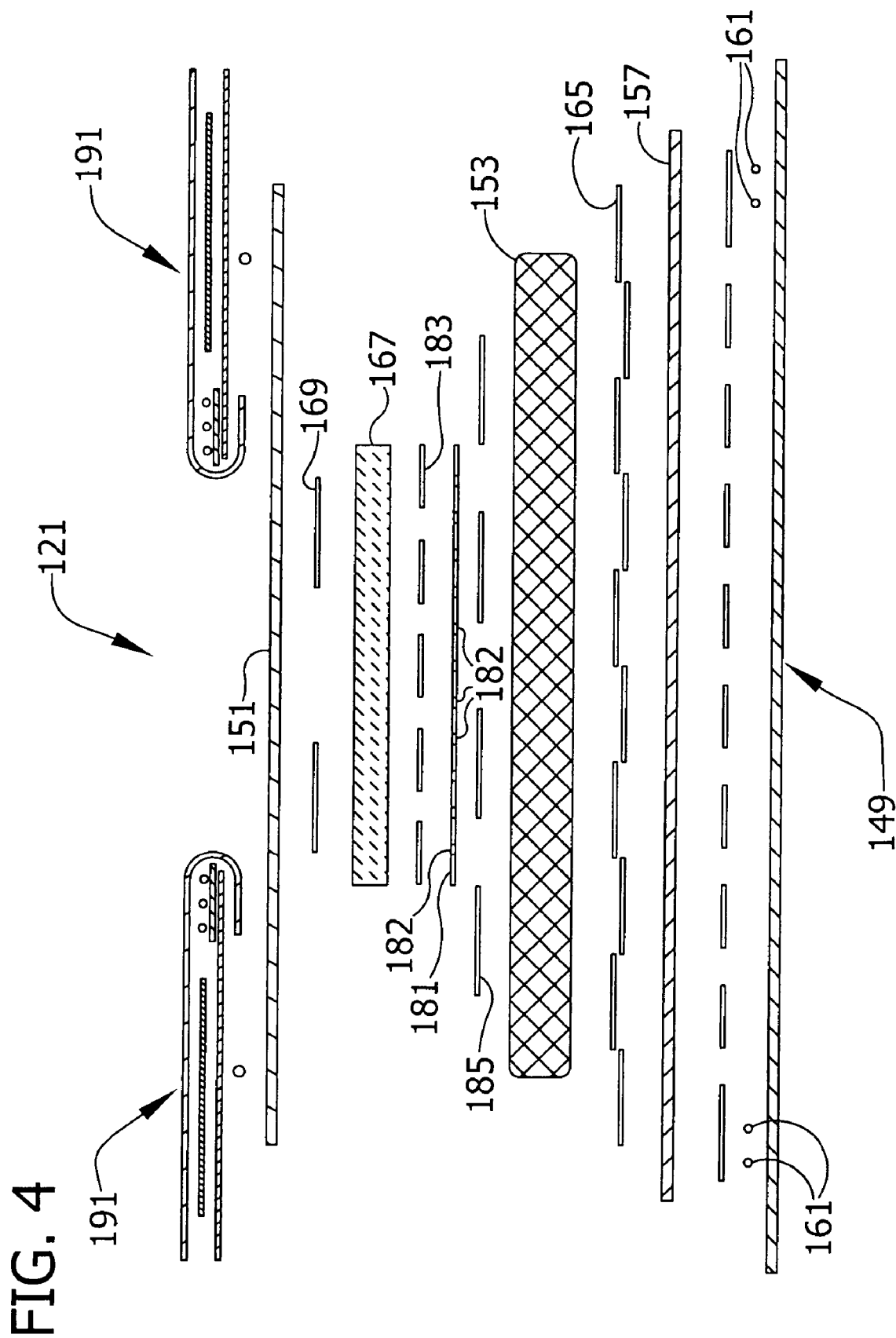
FIG. 4 is a separated cross-section taken laterally through a crotch region of training pants of a second embodiment of the present invention.

FIG. 4 illustrates training pants 121 of a second embodiment of the present invention which is substantially similar to the training pants 21 of the first embodiment in that it comprises an outer cover 149, a liner 151, an absorbent body 153 therebetween, side panels (not shown but similar to side panels 37, 39 of FIG. 2) and flaps 191. The absorbent body 153 is constructed to be generally compressible, pliable, non-irritating to the wearer's skin and capable of absorbing and retaining liquid body waste, such as urine. The absorbent body 153 may comprise hydrophilic fibers, such as a cellulosic fluff, mixed with particles of a high-absorbency material commonly known as superabsorbent material. More particularly, the absorbent body 153 may comprise a mixture of cellulosic fluff, such as wood pulp fluff, and superabsorbent hydrogel-forming particles. Alternatively, the absorbent body 153 may comprise only hydrophilic fibers, only superabsorbent material, or a combination of both along with other absorbent or non-absorbent materials.

One suitable type of wood pulp fluff is identified with the trade designation CR1654, available from U.S. Alliance, Childersburg, Ala., U.S.A., and is a bleached, highly absorbent sulfate wood pulp containing primarily soft wood fibers. However, the wood pulp fluff can be exchanged with other hydrophilic fiber materials, such as synthetic, polymeric, or meltblown fibers or with a combination of meltblown fibers and natural fibers. Suitable superabsorbent materials can be selected from natural, synthetic, and modified natural polymers and materials. The superabsorbent materials can be inorganic materials, such as silica gels, or organic compounds, such as cross-linked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany.

The absorbent body 153 may or may not be wrapped or encompassed by a suitable wrapping (not shown) which maintains the integrity and/or shape of the absorbent body. As shown in FIG. 4, the absorbent body 153 overlays the inner layer 157 of the outer cover 149, extending laterally between the leg elastic members 161, and is secured to the inner layer of the outer cover, such as by being bonded thereto with adhesive 165. However, it is contemplated that the absorbent body 153 may be unsecured to the outer cover 149 without departing from the scope of this invention.

A surge layer 167 lies between the bodyside liner 151 and the absorbent body 153 to help decelerate and diffuse surges or gushes of liquid body waste penetrating the liner. Desirably, the surge layer 167 can rapidly accept and temporarily hold the liquid body waste prior to slowly releasing the liquid body waste for flow toward the absorbent body. The surge layer 167 can include various types of fabrics, such as spunbond fabrics, meltblown fabrics, bonded carded webs, through-air bonded carded webs, knit fabrics, woven fabrics, airformed fabrics and the like, as well as combinations thereof. The fabrics can be composed of various types of fibers, such as polyolefin fibers, polyester fibers, bicomponent fibers, conjugate fibers, and the like, as well as combinations thereof.

For example, one suitable material from which the surge layer 167 can be constructed has a basis weight of about 50 gsm, and includes a through-air-bonded-carded web of a homogeneous blend of 60 percent 3 denier bicomponent fiber including a polyester core/polyethylene sheath, commercially available from KoSa Corporation of Salisbury, N.C., U.S.A., and 40 percent 6 denier polyester fiber, also commercially available from KoSa Corporation. Other examples of suitable surge layers 167 are described in U.S. Pat. Nos. 5,486,166; 5,490,846; 5,562,650; and U.S. Pat. No. 5,364,382, the entire disclosures of which are hereby incorporated by reference in a manner that is consistent herewith.

The surge layer desirably has a thickness of equal to or greater than about 1.5 mm, and a permeability in the range of about 2000-4000 darcies. The liner 151 is secured to the surge layer 167, such as by being bonded thereto using a suitable adhesive 169 and to the absorbent body, such as by being bonded thereto by additional adhesive 185. However, it is understood that the liner 151 may be unsecured to the surge layer 167 and/or to the absorbent body 153 without departing from the scope of this invention.

A flow control layer 181 lies between the surge layer 167 and the absorbent body 153 to retard the rate at which urine released from the surge layer flows toward the absorbent body. The flow control layer 181 shown in FIG. 4 has substantially the same width and length as the surge layer 167. However, it is understood that the flow control layer 181 may be narrower or wider than the surge layer 167, and it may be shorter or longer than the surge layer, without departing from the scope of this invention. The flow control layer 181 is secured on one side to the surge layer 167, such as by being bonded thereto by suitable adhesive 183, and is secured on its opposite side to the absorbent body 153, such as by being bonded thereto by the adhesive 185. While not shown in the drawings, it is contemplated that the flow control layer 181 may instead be wholly or partially wrapped around the absorbent body 153, particularly the portion of the absorbent body facing the liner 151 and surge layer 167.

The flow control layer 181 may be constructed of either an impermeable material or a permeable material, it being understood that the rate at which urine released from the surge layer 167 passes to the absorbent body 153 is generally a function of the permeability of the flow control layer. The permeability of the flow control layer 181 is desirably, although not necessarily, lower than the permeability of the surge layer. As an example, a suitable impermeable material from which the flow control layer 181 may be constructed is a polyolefin film that severely retards the flow of urine from the surge layer 167 to the absorbent body 153. Rather, urine released by the surge layer 167 is directed by the flow control layer 181 to migrate outward (e.g., within the surge layer) toward the peripheral edges of the flow control layer and then around the edges thereof to the absorbent body 153.

As another example, a suitable permeable material from which the flow control layer 181 may be constructed is a polypropylene or polyethylene film having apertures 182 formed therein to permit urine to flow therethrough. The apertures 182 are desirably sized in the range of about 1 mm-10 mm, and more desirably about 5 mm. The aperture density of the film is desirably less than or equal to about 14 apertures per square inch of the film and the thickness of the film is desirably less than or equal to about 0.003 inches (i.e., 3 mil).

Another suitable permeable material for construction of the flow control layer 181 is a meltblown, hydrophobic nonwoven material. The material desirably has a basis weight of about 0.6 ounce per square yard and a thickness of less than or equal to about 1 mm. It is also contemplated that the flow control layer 181 may be constructed of other permeable or impermeable materials, such as adhesive sprayed onto the bottom of the surge layer or the top of the absorbent body, with the thickness of the applied adhesive determining the permeability thereof, without departing from the scope of this invention.

When the wearer of the training pants 21 urinates therein, urine penetrates the liner 151 and is quickly taken into the surge layer 167. Urine is then released from the surge layer 167 for flow toward the absorbent body 153. The flow control layer 181 between the surge layer 167 and the absorbent body 153 retards the flow of urine to the absorbent body, causing unabsorbed urine to be maintained in the surge layer, such as in the interstitial spacings of the surge layer material, for a prolonged duration. Maintaining unabsorbed urine in the surge layer 167 facilitates the flow back of urine from the surge layer through the liner 151 to provide a desirably prolonged feeling of wetness against the wearer's skin, thereby providing an indication that urination has occurred. Eventually, urine flows through (if the flow control layer 181 is constructed of a permeable material) and/or around (if the flow control layer is constructed of an impermeable material) the flow control layer to the absorbent body 153 for subsequent absorption thereby to again provide a dry, comfortable feeling of the liner against the wearer's skin.

Figure 5:
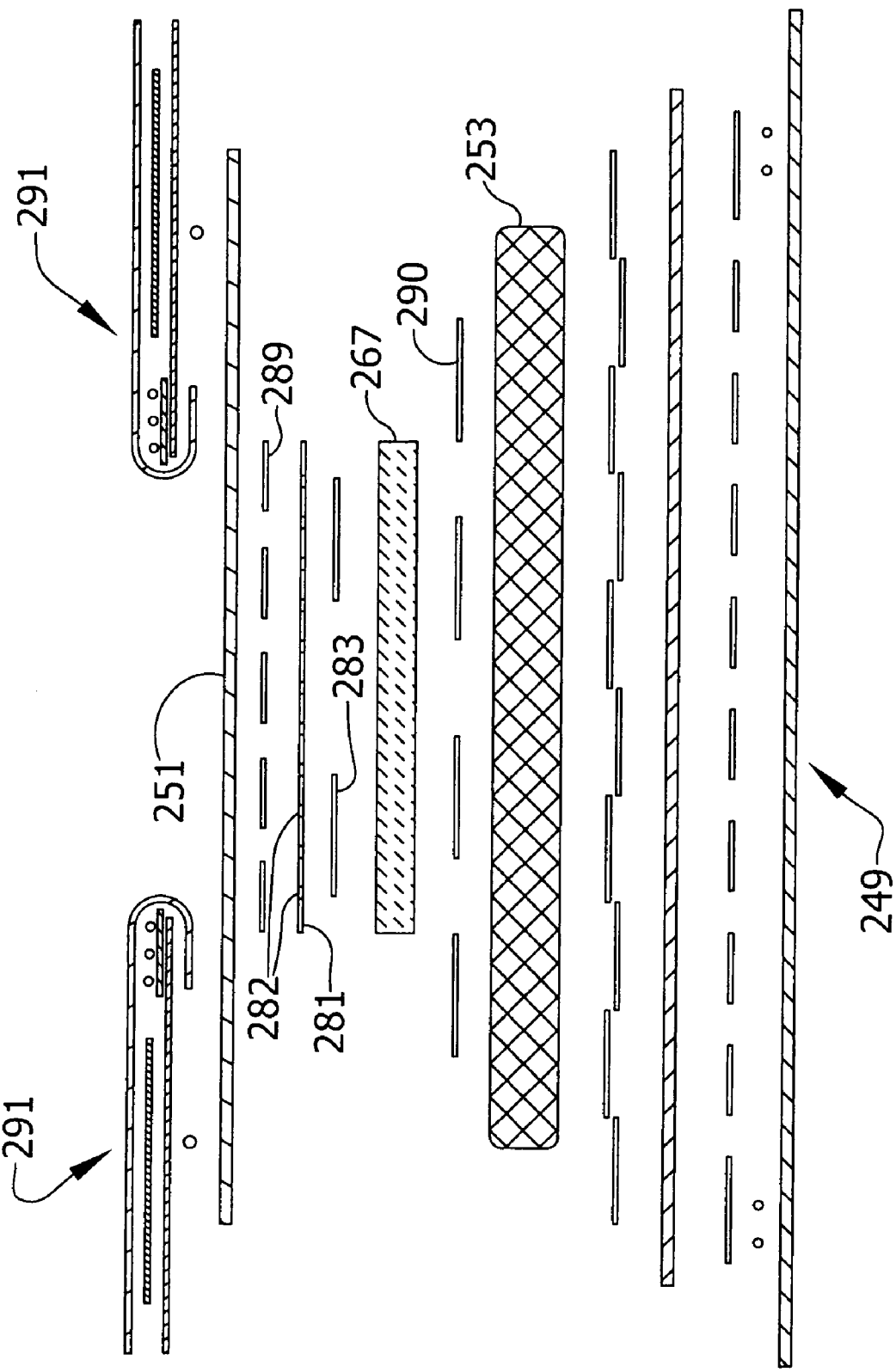
FIG. 5 is a separated cross-section taken laterally through a crotch region of training pants of a third embodiment of the present invention Corresponding reference characters indicate corresponding parts throughout the drawings.

FIG. 5 illustrates a third embodiment of training pants 221 which is substantially similar to the training pants 121 of the second embodiment in that it comprises an outer cover 249, a liner 251, an absorbent body 253 therebetween, side panels (not shown but similar to side panels 37, 39 of FIG. 2), flaps 291 and a surge layer 267. A flow control layer 281 overlays the surge layer 267, i.e., the flow control layer lies between the bodyside liner 251 and the surge layer. The liner 251 is secured to the flow control layer 281, such as by being bonded thereto using a suitable adhesive 289. The flow control layer 281 is secured to the surge layer 267, such as by being bonded thereto using a suitable adhesive 283, and the surge layer is secured to the absorbent body 253, such as by being bonded thereto with additional adhesive 290. However is understood that the surge layer 267 and the flow control layer 281 may be unsecured between the liner 251 and the absorbent body 253 without departing from the scope of this invention. Construction of the flow control layer 281 is substantially the same as that of the flow control layer 181 shown in FIG. 4 and described above in connection with the second embodiment of the training pants 121.

In use, as a surge of urine penetrates the liner 251, the flow control layer 281 retards the flow of urine to the surge layer 267. As a result, some of the urine may splash back against the wearer's skin while additional unabsorbed urine is maintained by the flow control layer 281 in the vicinity of the liner 251 to facilitate a prolonged feeling of wetness against the wearer's skin, thereby providing an indication that urination has occurred. Urine eventually flows through (if the flow control layer 281 is constructed of a permeable material) and/or around (if the flow control layer is constructed of an impermeable material) the flow control layer to the surge layer 267 and then the absorbent body 253 for absorption thereby to again provide a dry, comfortable feeling against the wearer's skin.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A disposable absorbent article for personal wear, the disposable absorbent article having a longitudinal direction and a lateral direction, said absorbent article comprising:

a generally liquid permeable liner having a bodyfacing surface;

an outer cover;

an absorbent body disposed between the liner and the outer cover for absorbing liquid body waste and having lateral side edges; and a flow control layer between the liner and the absorbent body, the flow control layer having lateral side edges, at least a portion of each lateral side edge of the flow control layer being spaced laterally inward from the lateral side edges of the absorbent body, the flow control layer being at least in part liquid impermeable to retard the flow of liquid body waste penetrating the liner toward the absorbent body whereby at least a portion of the liquid body waste that penetrates the liner is directed by the flow control layer to migrate laterally outward toward the lateral side edges of the flow control layer for subsequent flow around the flow control layer toward the absorbent body, the flow control layer being configured to permit at least some liquid body waste that passes through the liner to flow past the flow control layer toward the absorbent body without migrating laterally outward around the lateral side edges of the flow control layer, the flow control layer having a plurality of apertures, said apertures each being sized in the range of about 1 mm to about 10 mm.

2. A disposable absorbent article as set forth in claim 1 wherein the apertures each have a size of about 5 mm.

3. A disposable absorbent article as set forth in claim 1 wherein the flow control layer has an aperture density of less than or equal to about 14 apertures per square inch.

4. A disposable absorbent article as set forth in claim 1 wherein the flow control layer has a thickness of less than or equal to about 0.003 inches.

5. A disposable absorbent article as set forth in claim 1 wherein the flow control layer is secured to the liner.

\* \* \* \* \*